United States Patent
Griffin et al.

(10) Patent No.: US 9,700,565 B2
(45) Date of Patent: Jul. 11, 2017

(54) METHOD OF TREATING MIXED LINEAGE LEUKEMIA GENE-REARRANGED ACUTE LYMPHOBLASTIC LEUKEMIAS

(71) Applicants: James Douglas Griffin, Boston, MA (US); Doriano Fabbro, Alesheim (CH); Scott A. Armstrong, Boston, MA (US)

(72) Inventors: James Douglas Griffin, Boston, MA (US); Doriano Fabbro, Alesheim (CH); Scott A. Armstrong, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/928,223

(22) Filed: Oct. 30, 2015

(65) Prior Publication Data

US 2016/0184319 A1    Jun. 30, 2016

Related U.S. Application Data

(63) Continuation of application No. 14/311,834, filed on Jun. 23, 2014, now abandoned, which is a continuation of application No. 14/068,017, filed on Oct. 31, 2013, now abandoned, which is a continuation of application No. 13/606,070, filed on Sep. 7, 2012, now abandoned, which is a continuation of application No. 12/877,604, filed on Sep. 8, 2010, now abandoned, which is a continuation of application No. 10/596,708, filed as application No. PCT/US03/26629 on Aug. 25, 2003, now abandoned.

(51) Int. Cl.
*A61K 31/553* (2006.01)

(52) U.S. Cl.
CPC .................................. *A61K 31/553* (2013.01)

(58) Field of Classification Search
None
See application file for complete search history.

(56) References Cited

U.S. PATENT DOCUMENTS

| 7,011,947 B2 | 3/2006 | Golub et al. |
| 2002/0156033 A1 | 10/2002 | Bratzler |
| 2003/0125343 A1 | 7/2003 | Lecoutre |
| 2011/0009383 A1 | 1/2011 | Griffin |

FOREIGN PATENT DOCUMENTS

WO    WO-03037347 A1    5/2003

OTHER PUBLICATIONS

Armstrong et al. MLL translocations specify a distinct gene expression profile that distinguishes a unique leukemia. Nature Genetics, vol. 30, Published online Dec. 2001.
Structure-Activity Relationship and Drug Design, Remington's Pharmaceutical Sciences, pp. 420-425, 1980.
Armstrong, Scott A. et al. "Inhibition of FLT3 . . . ", Cancer Cell vol. 3, No. 2, pp. 173-183, Feb. 2003.
Armstrong, Scott A. et al. "Inhibition of FLT3 . . . ", Blood, vol. 100, No. 11, pp. abstract, Nov. 16, 2002.
Armstrong, Scott A. et al. Inhibition of FLT3 . . . , Proceedings of the American Association for Cancer Research Annual, vol. 44, pp. 1142, Jul. 2003.
Silverman et al. Newly diagnosed childhood acute lymphoblastic leukemia: update on prognostic factors and treatment. Curr. Opin. Hematol, 2003: 10: 290-296.

*Primary Examiner* — Anna Pagonakis
(74) *Attorney, Agent, or Firm* — Burns & Levinson, LLP; Daniel W. Clarke

(57) ABSTRACT

The present invention relates to a method of treating a warm-blooded animal, especially a human, having Mixed Lineage Leukemia (MLL rearranged ALL) comprising administering to said animal a therapeutically effective amount of a staurosporine derivative, especially PKC412 or a pharmaceutically acceptable salt thereof, alone or in combination with further therapeutic measures, for example, those defined herein; to the use of a staurosporine derivative for the preparation of a medicament for the treatment of MLL rearranged ALL; and to a commercial package comprising a staurosporine derivative together with instructions for its use in the treatment of MLL rearranged ALL.

3 Claims, No Drawings

METHOD OF TREATING MIXED LINEAGE LEUKEMIA GENE-REARRANGED ACUTE LYMPHOBLASTIC LEUKEMIAS

CROSS-REFERENCE TO RELATED APPLICATIONS

This application is a continuation application of U.S. Ser. No. 14/311,834, filed Jun. 23, 2014, which is a continuation application of U.S. Ser. No. 14/068,017, filed Oct. 31, 2013, which is a continuation application of U.S. Ser. No. 13/606,070, filed Sep. 7, 2012, which is a continuation application of U.S. Ser. No. 12/877,604, filed Sep. 8, 2010, which is a continuation application of U.S. Ser. No. 10/569,708, filed Feb. 27, 2008, which is a national stage application, filed under 35 U.S.C. §371 of International Application No. PCT/US03/26629, filed Aug. 25, 2003. The entire contents of each of which are hereby incorporated by reference in their entireties.

The present invention relates to a method of treating a warm-blooded animal, especially a human, having acute lymphocytic leukemia with rearrangement of the mixed lineage leukemia gene (hereinafter a disease state referred to as MLL rearranged ALL in this application) comprising administering to said animal a therapeutically effective amount of a staurosporine derivative, especially PKC412 or a pharmaceutically acceptable salt thereof, alone or in combination with further therapeutic measures, for example, those defined herein; to the use of a staurosporine derivative for the preparation of a medicament for the treatment of MLL rearranged ALL; and to a commercial package comprising a staurosporine derivative together with instructions for its use in the treatment of MLL rearranged ALL.

Characteristic for rearrangement of the mixed lineage leukemia gene is the co-expression of both myeloid and lymphoid antigens representative of a biphenotopic or mixed lineage derivation. In addition to their unique phenotypes, leukemias with rearrangement of the mixed lineage leukemia gene also display transcriptional programs distinct from those displayed by myeloid or lymphoid acute leukemias, respectively.

Surprisingly, it was found that staurosporine derivatives are useful for the treatment of MLL rearranged ALL.

Staurosporine derivatives which a suitable for the present invention, their preparation and suitable pharmaceutical formulations containing the same are described in EP 0 296 110, and, especially, in U.S. Pat. No. 5,093,330, which are herewith incorporated by reference.

Staurosporine derivatives and, in particular N-benzoyl-staurosporine has inhibitory effects on e.g. protein kinase C and FLT3 tyrosine kinase, especially on FLT3 tyrosine kinase when activating mutations are present. N-benzoyl-staurosporine is specifically disclosed as Example 18 of EP 0 296 110, has the International Non-proprietary Name MIDOSTAURINE and is also known as PKC412. Among the staurosporine derivatives, PKC412 or a pharmaceutically acceptable salt thereof, is especially preferred for use in accordance with the present invention.

It has now surprisingly been found that FLT3 is expressed at a relatively high level in MLL rearranged ALL, but it still remained unclear whether a constitutive FLT3 signal might be involved in the development and maintenance of MLL rearranged ALL. This is of particular importance since MLL rearranged ALL is very often a therapy-resistant form of leukemia.

Hence, the invention relates to a method of treating MLL rearranged ALL, comprising administering a therapeutically effective amount of a staurosporine derivative to a warm-blooded animal in need thereof, preferably of a therapeutically effective amount of PKC412.

It will be understood that in the discussion of methods, references to the active ingredients are meant to also include the pharmaceutically acceptable salts. If these active ingredients have, for example, at least one basic center, they can form acid addition salts. Corresponding acid addition salts can also be formed having, if desired, an additionally present basic center. The active ingredients having an acid group (for example COOH) can also form salts with bases. The active ingredient or a pharmaceutically acceptable salt thereof may also be used in form of a hydrate or include other solvents used for crystallization.

The term "treatment" as used herein comprises the treatment of patients having MLL rearranged ALL or being in a pre-stage of said disease which effects the delay of progression of the disease in said patients.

For the treatment of MLL rearranged ALL a staurosporine derivative can be administered alone or in combination with other forms of treatments, e.g. radiation therapy, in particular external radiation therapy or internal radiation therapy, or administration of other therapeutic agents.

The person skilled in the pertinent art is fully enabled to select relevant test models to prove the hereinbefore and hereinafter mentioned beneficial effects on MLL rearranged ALL of a staurosporine derivative. The pharmacological activity of a staurosporine derivative may, for example, be demonstrated in a suitable clinical study. Suitable clinical studies are, for example, open label non-randomized, dose escalation studies in patients with advanced MLL rearranged ALL alone or in combination with additional therapeutic measures, e.g., those mentioned herein. The beneficial effects on MLL rearranged ALL can be determined directly through the results of such studies or by changes in the study design which are known as such to a person skilled in the art.

The effective dosage of a staurosporine derivative may vary depending on the particular compound or pharmaceutical composition employed, the mode of administration, the type or development of the MLL rearranged ALL being treated, the severity of the MLL rearranged ALL being treated and the co-medication. Thus, the dosage regimen of a staurosporine derivative is selected in accordance with a variety of factors including the route of administration and the renal and hepatic function of the patient. A physician, clinician or veterinarian can readily determine and prescribe the effective amount of a staurosporine derivative required to prevent, counter or arrest the progress of the condition. Optimal precision in achieving concentration of the active ingredients within the range that yields efficacy without toxicity requires a regimen based on the kinetics of the active ingredients' availability to target sites.

In the present invention, PKC412 or a pharmaceutically acceptable salt thereof, can be administered twice or more daily, for example two or three times daily, on a continuous basis, alone, or during and subsequent to other therapies in reduced amounts. A daily oral administration of an amount in the range from 100 mg to 1000 mg, for example in the range from 100 mg/day to 750 mg/day or 150 mg/day to 500 mg/day, in particular 150, 225, 250, 300, 400 or 500 mg/day, split into two or more doses, is contemplated as a pharmaceutically effective amount in the daily regimen. A 150 mg/day dose is given as two 75 mg doses 6 to 12 hours apart, for example about 8 hours apart, and a 225 mg/day dose is administered as three 75 mg doses 6 to 8 hours apart.

Moreover, the present invention provides a commercial package comprising a staurosporine derivative, especially PKC412 or a pharmaceutically acceptable salt thereof, together with instructions for its use in the treatment of MLL rearranged ALL.

The present invention also relates to the use of a staurosporine derivative, especially PKC412 or a pharmaceutically acceptable salt thereof, for the manufacture of a medicament for the treatment of MLL rearranged ALL.

TEST TO DETERMINE IN VIVO ACTIVITY OF PKC412 AGAINST MLL REARRANGED ALL

To determine if PKC412 is effective against an in vivo model of MLL rearranged ALL, a xenograft model system in which leukemia burden can be quantitated with in vivo bioluminescent imaging is established. SEMK2-M1 and RS4; 11 (ATCC Number: CRL-1873) cell lines are engineered to express firefly luciferase fused to neomycin phosphotransferase by retroviral transduction. One million leukemia cells are then injected into the tail vein of SCID-beige mice. Within 1 week, the bioluminescent signal is detectable in a location consistent with the femur. Pathologic analysis of similarly xenografted mice confirm that the leukemia cells are initially found in the mouse bone marrow present in the femoral head. The leukemia subsequently progresses to replace the normal bone marrow and involve other organs, thus mimicking the progression of human leukemia. Once the leukemia had engrafted, as can be determined by the presence of a bioluminescent signal, a cohort of mice is treated with either 150 mg/kg PKC412 or vehicle once daily via gavage for 5 days per week. Serial imaging of the two cohorts is then performed to quantitate disease burden. In mice engrafted with SEMK2-M1 cells, quantification of total leukemic burden reveals anti-tumor efficacy of PKC412 after 2 weeks of therapy. The anti-tumor effect of PKC412 is specific for the cell line with activated FLT3 (i.e. SEMK2-M1 which over-expresses FLT3 due to gene amplification) as it has no effect on leukemia produced by injection of the cell line RS4; 11 which does not over-express FLT3. Pathological analysis performed at the completion of the study confirms the vast differences in tumor burden in SEMK2-M1 injected mice treated with PKC412 as compared to control mice. Thus, oral administration of PKC412 is effective in vivo against human lymphoblastic leukemia with an MLL rearranged ALL arrangement and activated FLT3.

What is claimed is:

1. A method of treating mixed lineage leukemia gene rearranged acute lymphoblastic leukemia (MLL rearranged ALL) in a human patient in need thereof comprising administering a therapeutically effective amount in the range from 100 mg/day to 1000 mg/day of PKC412, or a pharmaceutically acceptable salt thereof, to the human having MLL rearranged ALL.

2. The method according to claim 1 wherein the dose is in the range from 150 mg/day to 500 mg/day.

3. The method of claim 1 wherein the therapeutically effective amount is split into two or more doses per day.

* * * * *